(12) United States Patent
Fontana

(10) Patent No.: US 12,233,281 B2
(45) Date of Patent: Feb. 25, 2025

(54) THERAPEUTIC DEVICE FOR PAINFUL INFLAMMATORY PATHOLOGIES AND FOR NEURO-MUSCULAR AND NEURO-POSTURAL MODULATION

(71) Applicant: Fabio Fontana, Castelfranco Veneto (IT)

(72) Inventor: Fabio Fontana, Castelfranco Veneto (IT)

( * ) Notice: Subject to any disclaimer, the term of this patent is extended or adjusted under 35 U.S.C. 154(b) by 438 days.

(21) Appl. No.: 17/773,387

(22) PCT Filed: Oct. 28, 2020

(86) PCT No.: PCT/IB2020/060071
§ 371 (c)(1),
(2) Date: Apr. 29, 2022

(87) PCT Pub. No.: WO2021/084424
PCT Pub. Date: May 6, 2021

(65) Prior Publication Data
US 2022/0395698 A1    Dec. 15, 2022

(30) Foreign Application Priority Data

Oct. 31, 2019    (IT) .......................... 102019000020138

(51) Int. Cl.
| | |
|---|---|
| *A61N 5/06* | (2006.01) |
| *C09K 11/56* | (2006.01) |
| *C09K 11/65* | (2006.01) |
| *C09K 11/88* | (2006.01) |
| *B82Y 5/00* | (2011.01) |
| *B82Y 20/00* | (2011.01) |

(52) U.S. Cl.
CPC .......... *A61N 5/0622* (2013.01); *C09K 11/565* (2013.01); *C09K 11/65* (2013.01); *C09K 11/883* (2013.01); *A61N 2005/0631* (2013.01); *A61N 2005/0645* (2013.01); *A61N 2005/0661* (2013.01); *A61N 2005/0663* (2013.01); *B82Y 5/00* (2013.01); *B82Y 20/00* (2013.01)

(58) Field of Classification Search
CPC .... A61N 2005/0631; A61N 2005/0645; A61N 2005/0656; A61N 2005/0661; A61N 2005/0663; A61N 5/0622; B82Y 20/00
See application file for complete search history.

(56) References Cited

FOREIGN PATENT DOCUMENTS

| CN | 109568800 B | * | 9/2020 | ........... A61N 5/0613 |
| EP | 2422844 A1 | * | 2/2012 | ............... A61N 5/06 |
| WO | WO-2012019081 A2 | * | 2/2012 | ......... A61F 13/2097 |
| WO | WO-2018183835 A1 | * | 10/2018 | ....... A61F 13/00034 |

* cited by examiner

*Primary Examiner* — Jon Eric C Morales
(74) *Attorney, Agent, or Firm* — Collaborative IP; Paul Ditmyer

(57) ABSTRACT

The therapeutic device of the invention consists of a support to be placed on the skin of a patient and made of specific nanocrystals, which when properly activated, produce electromagnetic emissions that have beneficial effects on inflammatory, painful pathologies, and neuro-muscular and postural modulations of the patient.

17 Claims, 11 Drawing Sheets

Fig. 11

| | PRIMA /BEFORE T0 | T1 |
|---|---|---|
| Area $(mm^2)$ | 359 | 98,28 |
| Lunghezza (mm)<br>Length | 324,2 | 269,3 |
| Varianza di velocità<br>Speed variance | 25,09 | 9,859 |

THERAPEUTIC DEVICE FOR PAINFUL INFLAMMATORY PATHOLOGIES AND FOR NEURO-MUSCULAR AND NEURO-POSTURAL MODULATION

The object of the present invention relates to a device that allows you to treat painful, inflammatory pathologies, and also carry out a neuro-muscular and postural modulation.

STATE OF THE ART

The human body is known to be sensitive to electromagnetic radiation. One example of this sensitivity is demonstrated by the human body's ability to respond to sunlight through the synthesis of particular molecules. For example, stimulation of the human body in sunlight promotes the synthesis of vitamin D, which has a very important effect on the immune system, on the fixation of calcium in the bones, a bio-stimulation that accelerates the time of re-calcification.

Many of these biological phenomena are still being studied, and there are still several that have not been fully explored and understood.

However, based on certain natural effects, such as the exposure of the human body to solar radiation, attempts have been made to subject the human body, for therapeutic purposes, to very intense laser light, in order to obtain more significant effects, or at least equal to those obtained with solar radiation.

The results have not been very encouraging, and nowadays therapies using laser light use much more limited and lower intensities.

Nevertheless, exposure to these lasers is always of a rather short duration, since the bulky machines in treatment centres need to be available to a large number of patients.

Furthermore, it has been seen that the frequency of the light emitted by these lasers is specific to the purpose of the treatment. So the treatment of a patient who has several pathologies, or who has various therapeutic failures should be treated with different laser emissions and in various treatment sessions.

They also exist in the field of electronic components that, when stimulated by specific wavelengths, emit photons in selected wavelengths. These components are used for creating photovoltaic panels and for making nanocrystal video displays.

Nobody would ever have thought that these components could be used in the therapeutic area, also because most of them, although they have frequencies quite close those of interest, have a completely different field and method of use.

For a long time, infrared irradiation of people's skin has been used for physiotherapy applications with an emission frequency in the low infrared, i.e. between 760-1500 nm, exploiting the thermogenetic effect and with very high emission powers generated by 150-1500 W infrared lamps.

It has been found that such heating is generally not tolerated since it is too intense.

Furthermore, the purposes of such treatments are to heal only the surface layer of the epidermis, even if they are called physiotherapy applications.

It has recently been found that patients can much more easily tolerate the use of lasers and/or nanocrystals, again for physiotherapy applications, in the low infrared range with 1100-1400 nm emission frequencies. However, these applications require close and continuously active sources for exciting the nanocrystals, which can reach up to 50 W.

This need for such powerful excitation lamps makes the aforementioned devices dependent on a fixed power source and, therefore, they are not transportable. Therefore, treatment with such nanocrystal and/or laser-based devices is limited in time to just the time of infrared irradiation applications at healthcare facilities that have the aforementioned equipment.

A further application of lasers or nanocrystals in the therapeutic treatment of the surface layer of the skin, in fact it has been confirmed that a wavelength between 613 and 846 nm can be effective in the treatment of skin abrasions However, such patches can only be an effective treatment when they are exposed to the light of the external environment that irradiates the outer surface of said patches. However, these patches, in order to have a significant therapeutic effect, raise the temperature of the skin, and in fact the nanocrystal emission field is in the low infrared and are not tolerated do not tolerate lengthy exposure to the external environment, causing a reddening of the underlying part of these patches and an inflammation of the abrasion. For this reason, the nanocrystals are dispersed at a distance from one another, allowing ambient light to pass through the spaces between the nanocrystals. In the event that they are applied to the patient's skin, but are hidden underneath clothing that prevents the patch from receiving ambient light on their outer surface, said nanocrystals do not emit any radiation to treat the abrasion of the skin.

In the context of the aforementioned application of the patches employing nanocrystals, there are also bandages or other devices that when applied to the patient's skin are effective in treating the exposed and external parts of a person. The outer part of said bandages or other devices, with respect to the part resting on the person, must be hit by radiation coming from the outside and emit therapeutic radiation towards the skin; however, such devices seem to be very ineffective, and indeed, they require:

an external area for collecting the incident radiation from the outside, guide devices for directing the incident radiation precisely towards said nanocrystals that emit a specific frequency through an emission area;

requiring, in order to function, that said external incident area is greater than the emission area, and finally requiring further devices for increasing the proportion of the electromagnetic radiation received by the collector surface that is transmitted to said guide devices.

However, these devices are not suitable for being constantly attached to the body, so they must be periodically removed, for example to go to bed.

Evidently therefore, due both to the modest effectiveness of the radiation, and also the need for constant illumination from the outside to function, and because it is impossible to keep it constantly in contact with the body, but above all because a much larger surface than the surface of treatment is required, said bandages are unsuitable for continuously treating internal pathologies of a person's body at ultra-low powers.

A further and different application involves the use of nanocrystals for use in phototherapy, requiring a special LED emission source that the nanocrystals convert into specific wavelengths.

However, these applications do not specify the power of the emission both for the LED sources and for the nanocrystals, thus leaving the user with an arbitrary choice, which in most applications renders the treatment ineffective due to excessive irradiation. Many users feel uncomfortable with a treatment that includes irradiation with a low infrared wavelength component, especially for intensities greater than 1 mW/cm2. Even in this additional and different application, there is no continuity of the ultra-low power treatment of internal pathologies of a person's body.

OBJECTS OF THE INVENTION

The object of the present invention is to make available a therapeutic or healing device that can be easily employed for health benefits for the human body.

Another object of the present invention is to make available a therapeutic device that can be effective for most people who have acute pain or inflammation.

A further object of the present invention is to make available an effective therapeutic device that can easily be adapted.

Another object of the present invention is to make available a therapeutic device that can be constructed inexpensively and that requires little maintenance, and that also has low energy consumption.

A further object of the present invention is to make available a therapeutic device that is particularly effective with regard to muscle detensioning.

Another object of the present invention is to make available a therapeutic device that is particularly effective in postural modulation.

An important object of the present invention is to make available a therapeutic device that provides long-term effects without any appreciable electrical expenditure during the treatment.

Another important object of the present invention is to make available a therapeutic device that can be used without incurring any deterioration.

A different object of the present invention is to make available a therapeutic device that can function even without being directly irradiated by an external source.

Yet another object of the present invention is to make available a device that has a synergistic and combined effect for therapeutic treatment.

An important object of the present invention is to provide a device whose specific emission power cannot inflame the skin of a person's body and, therefore, can be kept in contact with the skin continuously, even for days and even during the night.

EXPLANATION OF THE INVENTION

All the aforementioned objects, and others which will be more fully apparent from the following explanation, are attained by the device of the invention in accordance with the following description.

The invention consists of a therapeutic device comprising at least one supporting laminar element (hereinafter also just: support) and the combination of at least two quantum dots, from among the following:

Graphene quantum dots Code 900708 or quantum dots with a fluorescence indicatively corresponding to: λex 350 nm, λem 445 nm, FWHM 65 nm, quantum yield >65%

Graphene quantum dots blue luminescent Code 900726 or quantum dots with a fluorescence approximately corresponding to: λex 350 nm; λem 445 nm±10 nm, FWHM 75 nm, quantum yield ≥20%

Graphene quantum dots cyan luminescent, Code 900707 or quantum dots with a fluorescence indicatively corresponding to: λem 475-495 nm, FWHM 70 nm, quantum yield >17%

Graphene quantum dots aqua green luminescent, Code 900712 or quantum dots with a fluorescence indicatively corresponding to: →l λex 485 nm; λem 530 nm±10 nm, FWHM 80 nm, quantum yield ≥17%;

Perovskite quantum dots oleic acid and oleylamine coated, Code 900747 or quantum dots with a fluorescence indicatively corresponding to: λem 480 nm;

CdTe core-type quantum dots COOH functionalised Code 777978 or quantum dots with a fluorescence indicatively corresponding to: λem 710 nm, quantum yield ≥15%;

CdS/ZnS core-shell type quantum dots oleic acid functionalised Code 900286 or quantum dots with a fluorescence indicatively corresponding to: λmax 385 nm λem 400 nm±10 nm, quantum yield >50%;

CdS/ZnS core-shell type quantum dots oleic acid functionalised Code 900283 or quantum dots with a fluorescence indicatively corresponding to: λmax 405 nm λem 425 nm±10 nm;

where said support is composed of a laminar element made of a material transparent at the reference wavelengths and at the wavelength of the radiation emitted by the human body, where a first side of the laminar support is suitable for coming into direct contact with the skin of the person whose disorder or inflammatory pathology is to be treated, and where there is, on the opposite side of the first side of said support, or incorporated into or diffused into the laminar element itself, a mixture of at least two of said quantum dots, with a concentration from 1 mg/cm2 to 100 mg/cm2, capable of emitting photons in the reference wavelength, with an intensity between 0.1 mW/cm2 and 0.5 mW/cm2, and preferably between 0.2 mW/cm2 and 0.4 mW/cm2 and where said reference wavelength is between 280 and 740 nm, and preferably between 350 nm and 530 nm when stimulated by at least infrared, light or ultraviolet electromagnetic radiation.

ADVANTAGEOUS CHARACTERISTICS OF THE INVENTION

Advantageously, said support consists of a material transparent to at least an infrared, light or ultraviolet electromagnetic radiation, where the radiation has a wavelength that can excite the aforementioned mixture of quantum dots, and where the very body heat itself of the patient, understood as electromagnetic emission in the infrared spectrum, and other electromagnetic emissions of the human body including UV, to excite said quantum dots.

Advantageously, said support consists of a plastic material that can connect with the patient's epidermis, without deteriorating due to the sweat emitted by the skin, and without allowing it to migrate through said support, since said sweat can cause a quantum dot or the mixture of quantum dots to deteriorate.

Advantageously, said support is composed of a flexible material that can connect with the epidermis of the patient and follow the skin's movements and/or deformations without coming off, where said support preferably has a thickness of between 0.05 mm and 2 mm, and even more preferably between 0.1 and 1 mm, being able to better adapt to deformations of the epidermis.

Advantageously, said mixture of quantum dots is distributed on the support so they occupy most of the surface of the side on which the mixture is applied, like a varnish, using the whole surface for a highly efficient transmission of said radiation, without being hindered by an overlapping of the quantum dots, with a thickness between 0.001 and 1 mm.

Advantageously, said mixture of quantum dots is arranged on the support in discrete zones, concentrating the flow of the radiation in defined areas, in order to be intense enough to be absorbed through said support, with thicknesses ranging from 0.005 to 1 mm.

Advantageously, said laminar support element (hereinafter also only support) is joined to a second laminar protection and confinement element (hereinafter also only protection or protection element), containing and confining said mixture of quantum dots, protecting it from external agents or mechanical stresses that would ruin it.

Advantageously, said second laminar element is composed of a material transparent to infrared radiation or light radiation in the visible or ultraviolet spectrum, so that the radiation coming from the outside and passing through said second laminar element can excite said mixture of quantum dots so that they emit the required frequencies.

Advantageously, said protection, with an extension comparable to the extension of the support, is joined to it with the surface of its side facing the support retaining and hermetically sealing mixture of quantum dots.

Advantageously, the protection consists of a protective transparent ink or a plastic film that can reduce the thickness of the device and making it easier to wear.

Advantageously, said mixture of quantum dots is diluted in an ink so that it can be printed on the support or on the protection, directly on the sides facing each other, making it easier to position and arrange said mixture of quantum dots.

Advantageously, said ink is a transparent ink, so that only the characteristics of the adhesive and the ink are in the dispersion medium, and that all the outgoing photon emissions and the incoming radiations can reach the mixture of quantum dots with minimal attenuation.

Advantageously, the device has a minimum thickness in order to maintain a high degree of elasticity and so that it can adapt to the surface stresses of the skin without cracking, breaking or tearing.

Advantageously, the connection of the dermis and the support and/or the support and the protection is obtained using a flexible double-sided tape, providing great deal of freedom when choosing the support and/or the protection materials, with regard both to the material they are made of and their thickness.

Advantageously, said double-sided adhesive material, at least along all the perimeter edges of the device, between the support layer and the protection layer, manages to effectively contain the mixture of quantum dots, preventing a dispersion of said quantum dots outside the device itself, and preventing the nanotechnological material contained in the device, and that has escaped from it, from coming into contact with the user's skin.

Advantageously, said device is laser cut from a polylaminate sheet, therefore said laser cutting can carry out a perimeter sealing of the edges of the device in its multiple layers, constituting a hermetic seal keeping the quantum dots within the device, and preventing any dispersion outside.

Advantageously, the fact that the device can be mostly transparent, and adhering to the skin, placed near primary and secondary endings, tendons, muscles, dermatomers, nerve endings, to favour a neuro-muscular and postural modulation, it makes it possible to check for any redness of the skin.

Advantageously, the wearable therapeutic device provides greater activity of the mixture of quantum dots with an ink comprising from 5 to 80% carbon nanotubes, with a mixture of quantum dots from 95 to 20%, depending on the type of quantum dots used and the frequency of the therapeutic radiation, managing to calibrate, redefine and dose the quantity of photons emitted by the device according to the needs of the patient and the stimulus that you want to obtain.

Advantageously, the mixture of quantum dots comprises two or more of the following quantum dots:

Graphene quantum dots Code 900708 or quantum dots with a fluorescence indicatively corresponding to: $\lambda ex$ 350 nm; $\lambda em$ 445 nm, FWHM 65 nm, quantum yield >65%;

Graphene quantum dots blue luminescent Code 900726 or quantum dots showing a fluorescence approximately corresponding to: $\lambda ex$ 350 nm; $\lambda em$ 445 nm±10 nm, FWHM 75 nm, quantum yield ≥20%

Graphene quantum dots cyan luminescent, Code 900707 or quantum dots showing a fluorescence indicatively corresponding to: $\lambda em$ 475-495 nm, FWHM 70 nm, quantum yield >17%

Graphene quantum dots aqua green luminescent, Code 900712 or quantum dots showing a fluorescence indicatively corresponding to: $\lambda ex$ 485 nm; $\lambda em$ 530 nm±10 nm, FWHM 80 nm, quantum yield ≥17%;

Perovskite quantum dots oleic acid and oleylamine coated, Code 900747 or quantum dots showing a fluorescence indicatively corresponding to: $\lambda em$ 480 nm;

CdTe core-type quantum dots COOH functionalized Code 777978 or quantum dots showing fluorescence indicatively corresponding to: $\lambda em$ 710 nm, quantum yield ≥15%;

CdS/ZnS core-shell type quantum dots oleic acid functionalised Code 900286 or quantum dots showing a fluorescence indicatively corresponding to: $\lambda max$ 385 nm $\mu em$ 400 nm 10 nm, quantum yield >50%;

CdS ZnS core-shell type quantum dots oleic acid functionalised Code 900283 or quantum dots showing a fluorescence indicatively corresponding to: $\Lambda max$ 405 nm $\lambda em$ 425 nm±10 nm;

allowing the same wavelengths as ULLLT (ultra-low-level laser therapy) to be attained and produced but at an ultra-weak intensity, without saturation effects due to an excessive intensity of the photonic emission flow of the quantum dots mixture and without the side effects of conventional laser or light therapy.

Said quantum dots are therefore also defined as upconverting nanocrystals. These and other objects are all attained by the device of this invention according to the attached claims.

EXPLANATION OF THE INVENTION

The therapeutic device for painful and/or inflammatory pathologies and for a neuro-muscular and postural modulation, the object of the invention, is a device that is based on a technology that exploits the ability of nanometric-sized crystals that can, if appropriately stimulated, emit photons in a precise frequency, specific to each of the quantum dots. These photons emitted in a precise frequency range, as an example of one of the aforementioned benefits, stimulate the human body to achieve neuro-muscular rebalancing. Only the combination of two or more electro-magnetic emissions of the claimed quantum dots mixture obtains a synergistic effect of all or part of the above-mentioned advantages: in decreasing the acute inflammatory state, and/or modulating the neuro-muscular energy state, and/or modulating the postural structure, all aspects that would not be found with the use of a single quantum dot or the individual families of the quantum dots mixture.

Furthermore, it has been verified that only a therapeutic device that can be effective with a continuous application over time, to be continuously active and resting against the person's skin, for example for one or more days, including night, and with an ultra-weak power, namely, less than 0.5 mW/cm2 of the emission intensity, can achieve the efficacy of the therapeutic treatment described above.

While a device that has a gap in the treatment and/or an intensity higher than the emission intensity described above achieves a saturation effect and sometimes inflammation, and therefore contrary to the therapeutic effect of the device of the invention, and of the biological principles of cellular stimulation through electromagnetic radiation.

In addition, prolonged exposure of infrared and low infrared radiation, for example using quantum-dots in the frequency above 760 nm, inevitably leads to localised inflammation and, furthermore, people do not easily tolerate such devices because of the continuous and persistent sensation of a hot spot.

BRIEF DESCRIPTION OF THE DRAWINGS

The technical characteristics of the invention, according to the aforesaid objects, can clearly be seen in the claims below, and its advantages will become more readily apparent in the detailed description that follows, made with reference to the accompanying drawings, which illustrate a preferred embodiment, which is purely exemplary and not limiting, in which:

FIGS. 9-11 are a graphical representation of a stabilometry, before and after the application of the device of the invention, and a table that highlights the usefulness of the device of the invention for postural modulation.

DETAILED DESCRIPTION OF AN EXAMPLE OF A PREFERRED EMBODIMENT

Figure 1:
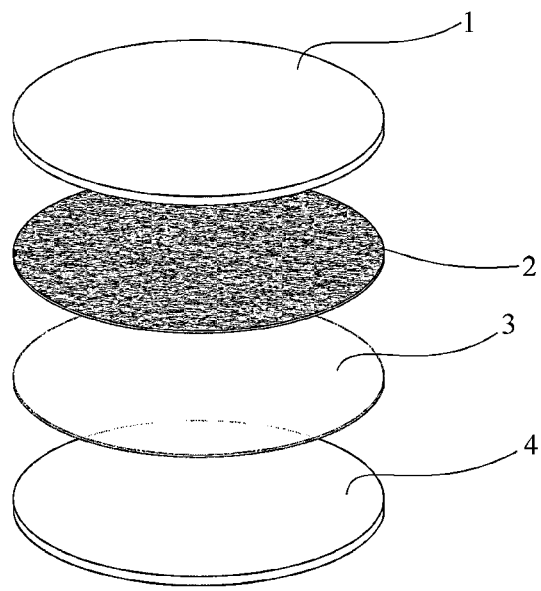
FIG. 1 shows an example of the device of the invention.
Figure 2:
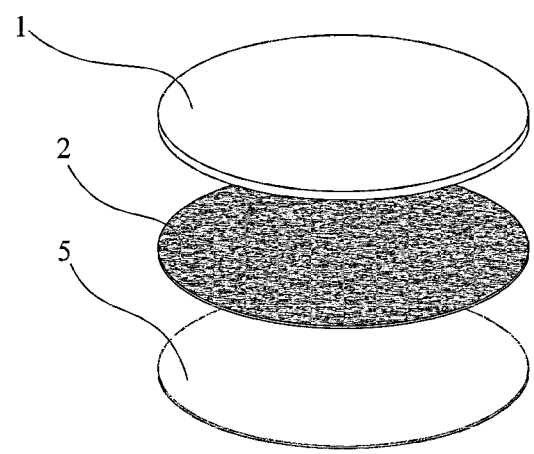
FIG. 2 shows a modified embodiment of the device of the invention

With reference to the figures, the device of the invention consists of two laminar layers of transparent plastic, the transparent insulating plastic laminar element 1 and the insulating transparent plastic laminar element 4, preferably flexible, a first one with a supporting function and a second one with protective and insulating function, which enclose and confine a mixture of quantum dots 2.

Generally, this mixture also includes a percentage of carbon nanotubes, in order to arrive at the precise percentage of this mixture of quantum dots 2, and also due to their conductive effect, which allows the radiation to be received that stimulate the quantum dots and therefore the photonic emissions of said mixture to be transmitted outside the device.

To facilitate the printing on a wall between the two outer layers of the mixture of quantum dots, the mixture is dispersed in a transparent ink.

To ensure the flexibility of the device and to prevent the two outer layers 1, 4 separating, a double-sided adhesive 3 is used, preferably suitable for coming into contact with a person's skin, which retains two layers 1, 4 that are joined together, including the mixture of quantum dots 2.

To render said device even more flexible, the outer layers are limited to a thickness of a few tenths of a millimetre to a few millimetres, preventing breakage or cracking following significant bending.

This flexible double-sided adhesive 3 also makes it more reliable over time, having a modulus of elasticity greater than the layers, but the adhesive allowing possible sliding between the layers of the composite device.

The wall of the support 1 that will come into contact with the patient's skin is applied, either directly or with the interposition of a removable plaster, onto the skin to be treated.

The points where said device is to be applied are precisely established on the skin or on the nerve centre: they are the primary and secondary nerve endings of tendons, muscles, dermatomes and nerve endings, where you want to encourage the neuro-muscular and postural modulation, painful and inflammatory.

The very modest size of these emissions, comparable to an intensity of ULLLT (ultra low level laser therapy), to the fact that they are continuously applied (even for 24 hours a day) and that they are a combination of emissions centred precisely on the wavelength required, the effects and results of the invention can be obtained.

In fact, only thanks to the combination of the emissions that provide detensioning, reducing the pain, and the emissions that treat the neuro-muscular modulation, is it possible to get long-lasting and effective results.

Figure 3:
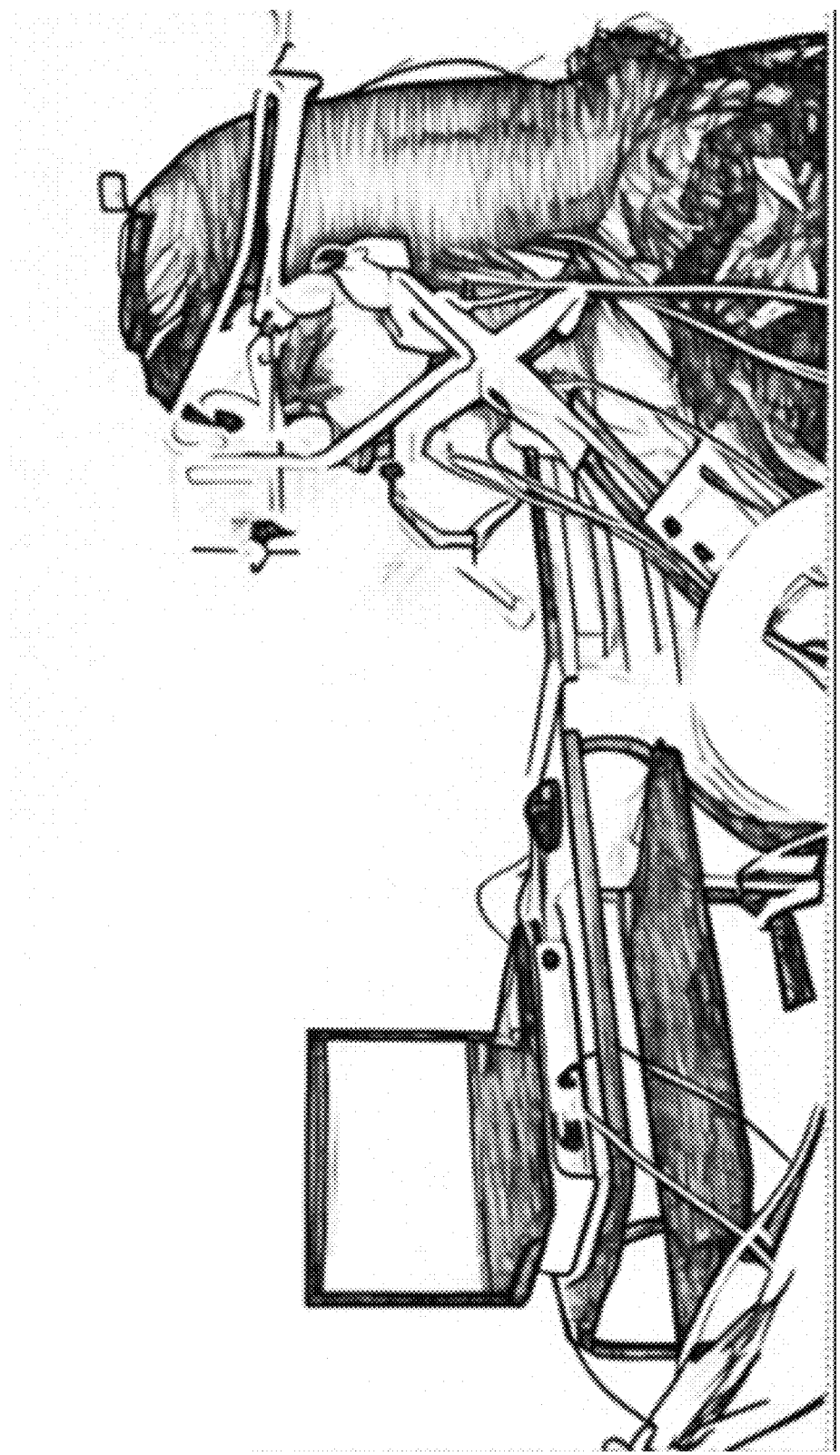
FIG. 3 shows the patient undergoing treatment during data acquisition
Figure 4:
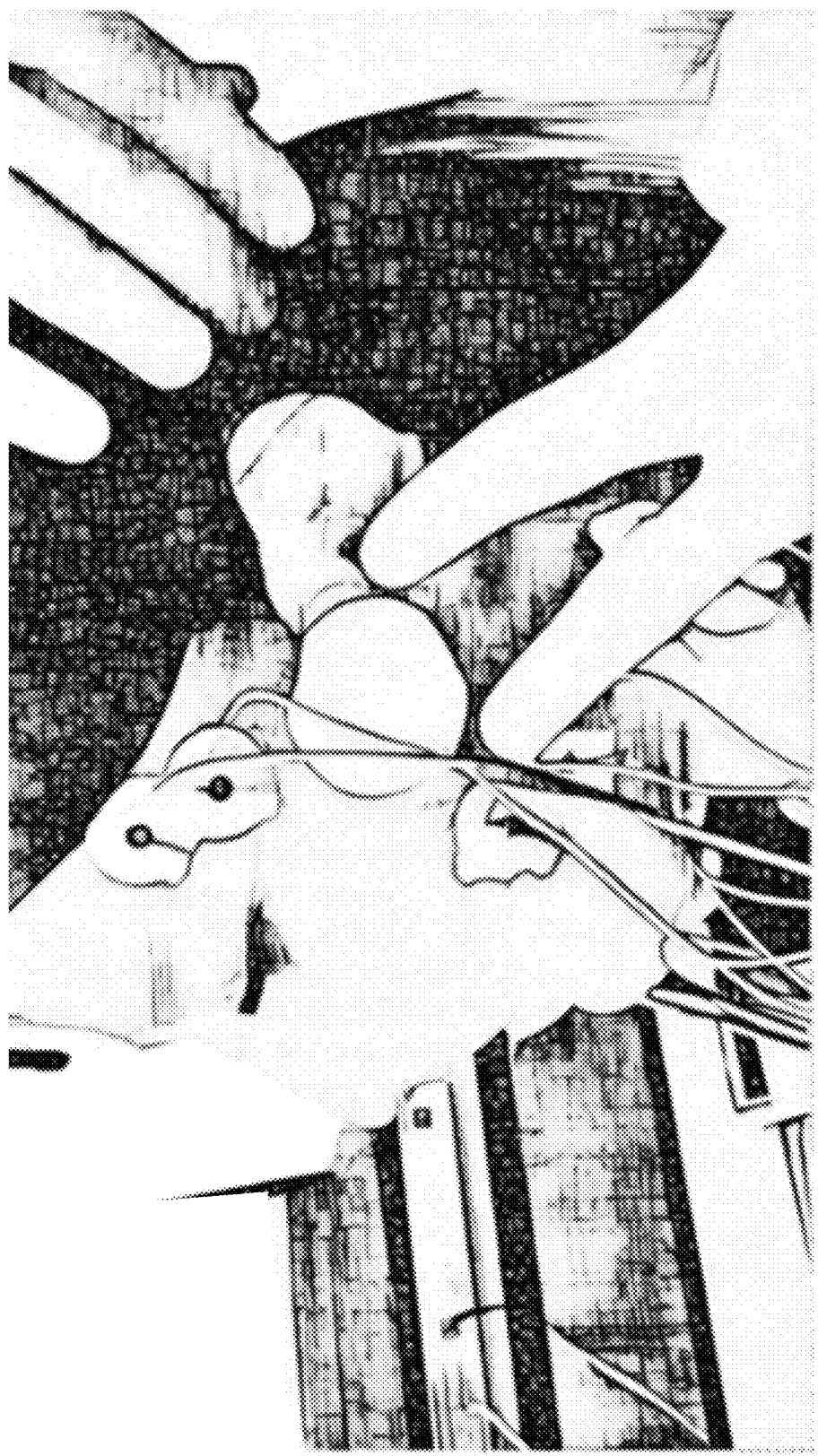
FIG. 4 shows the use of the device of the invention with the same patient
Figure 5:
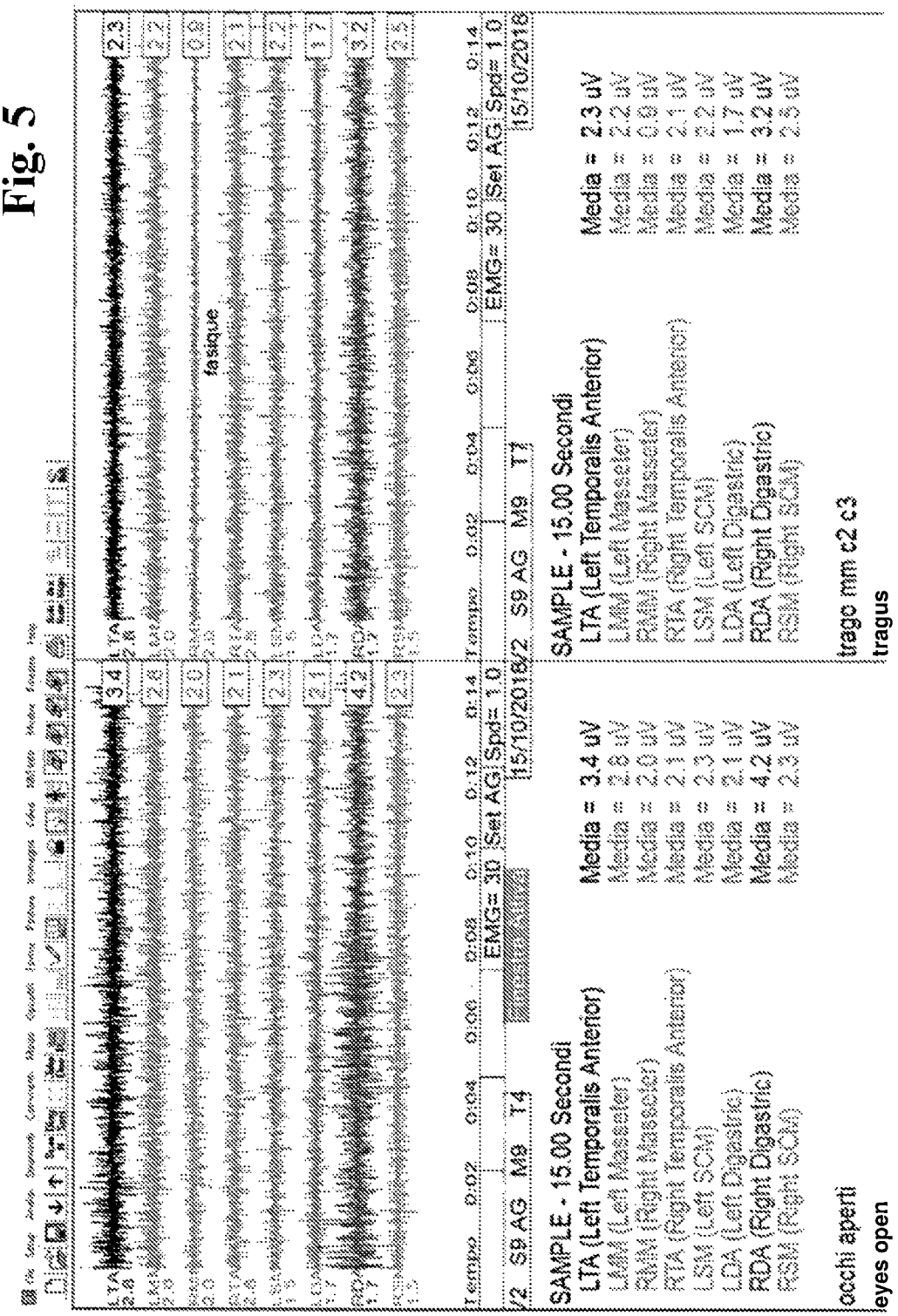
FIG. 5 shows the chart of the values obtained by means of advanced medical diagnostic instrumentation EMG and K7 Kinesiograph, in a comparative way, before and after the use of the invention.

First Example of an Application (FIGS. 3-5)

By way of a non-limiting example, here is an application aimed at neuro-muscular modulation in a patient with tense chewing muscles.

These figures show how EMG electromyography (K7) is carried out on a patient with temporomandibular joint dysfunction, evaluated by a gnathologist dentist with and without devices of the invention.

All the measurement values of the left screen were collected before the application and the measured values of the right screen were collected a few minutes after the application of the devices of the invention.

Values above 2.4 uV are considered excessive muscular response/tension.

As can be seen from the legend, all the muscles treated RMM (Right Masseter), LMM (Left Masseter), LTA (Left Temporalis Anterior), RTA (Right Temporalis Anterior), LSM (Left SCM), RSM (Right SCM), had a reduction in resting tension measured using the electrical activation of the EMG muscle.

We can see a normalisation of muscular activation at rest, managing tensions on the patient.

Figure 8:
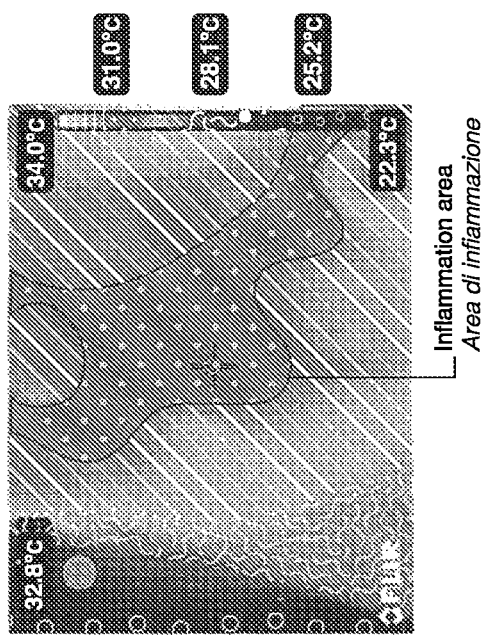
FIGS. 6-8 are photos of thermographs of inflamed parts, in the infrared and visible spectrum, and a thermograph of the same part 24 hours after use of the device of the invention.
Figure 7:
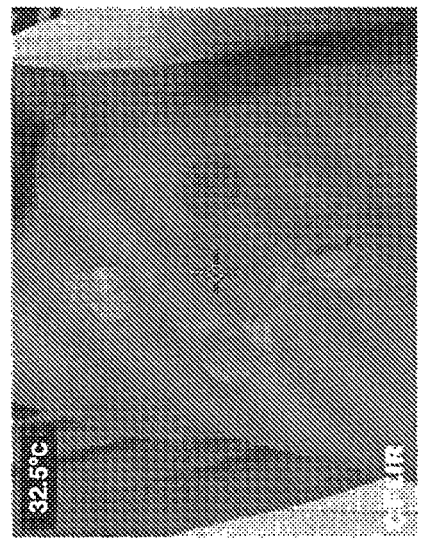
Figure 6:
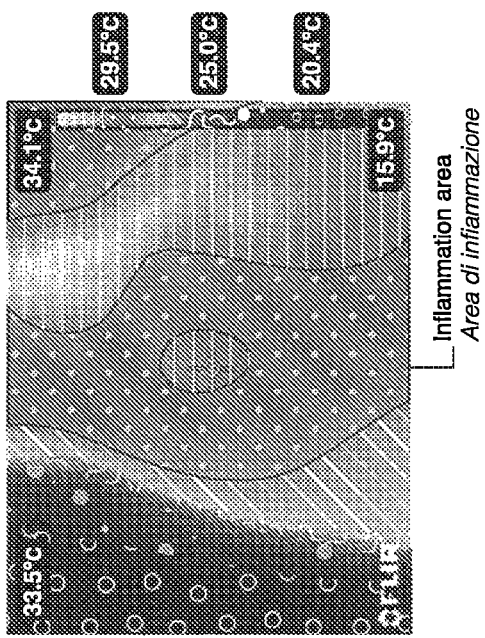

In the left chart without devices, in fact, many muscles are overstimulated, i.e. they have values greater than 2.3 uV at rest with an average of 2.6 uV In the right chart we carry out the measurement after applying the devices with a symmetrical protocol, we can see an substantial normalisation of the patient with most of the muscles that already after just a few minutes drops below 2.4 uV with an average of 2.1 uV Second Example of an Application (FIGS. 6-8)

FIG. 6 shows a thermograph of inflammation created by a partial lesion of the tendon of the right rectus femoris of an Italian Serie A footballer.

We can see in FIG. 8, (thermographic view in FIG. 8 and corresponding visible view in FIG. 7) referring to the same limb of the same patient of the thermograph of FIG. 6, the reduction of the inflammation and the inflammation area 24 after the application of some devices of the invention suitably placed near the inflamed part.

Figure 9:
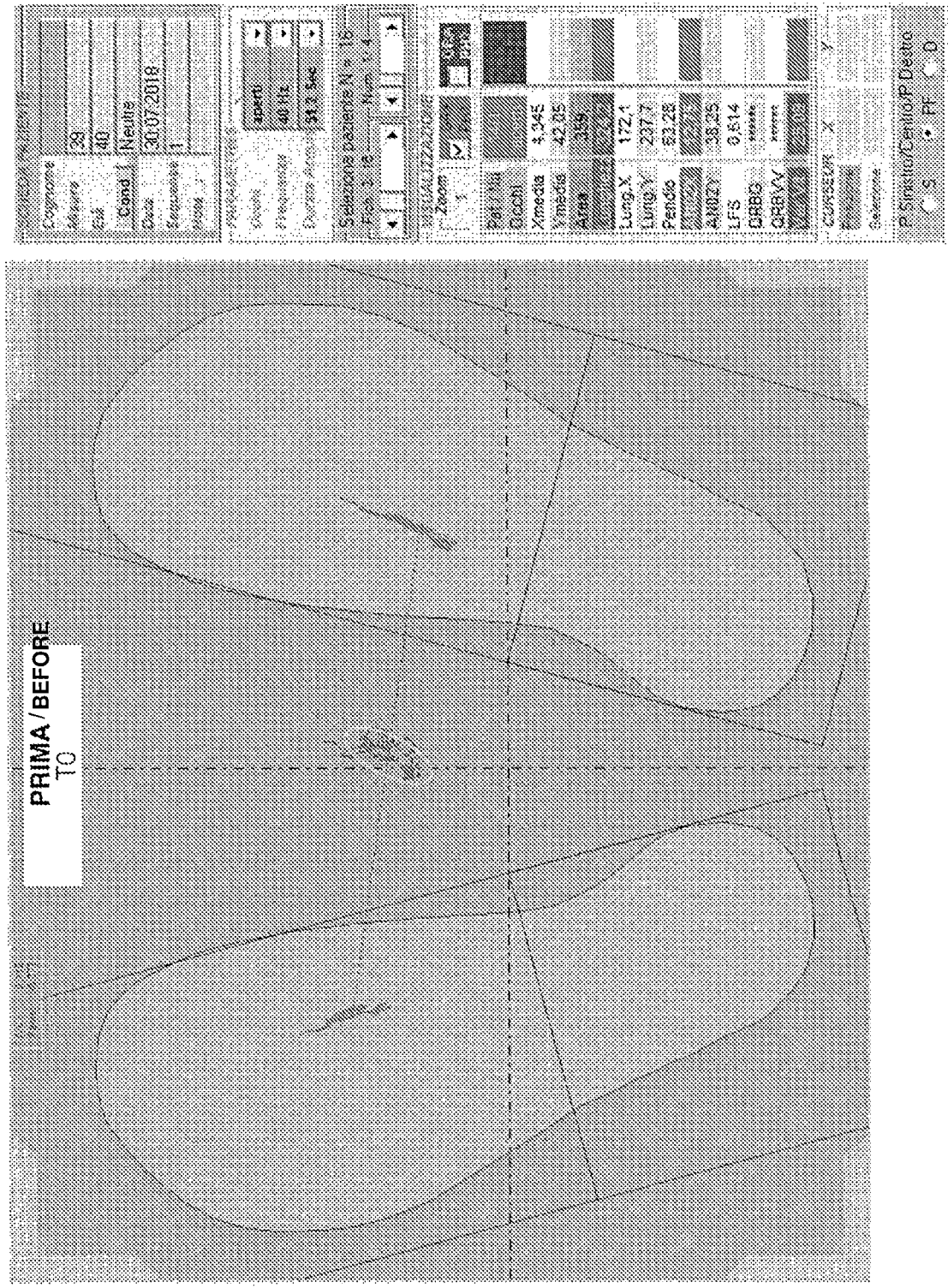
Figure 10:
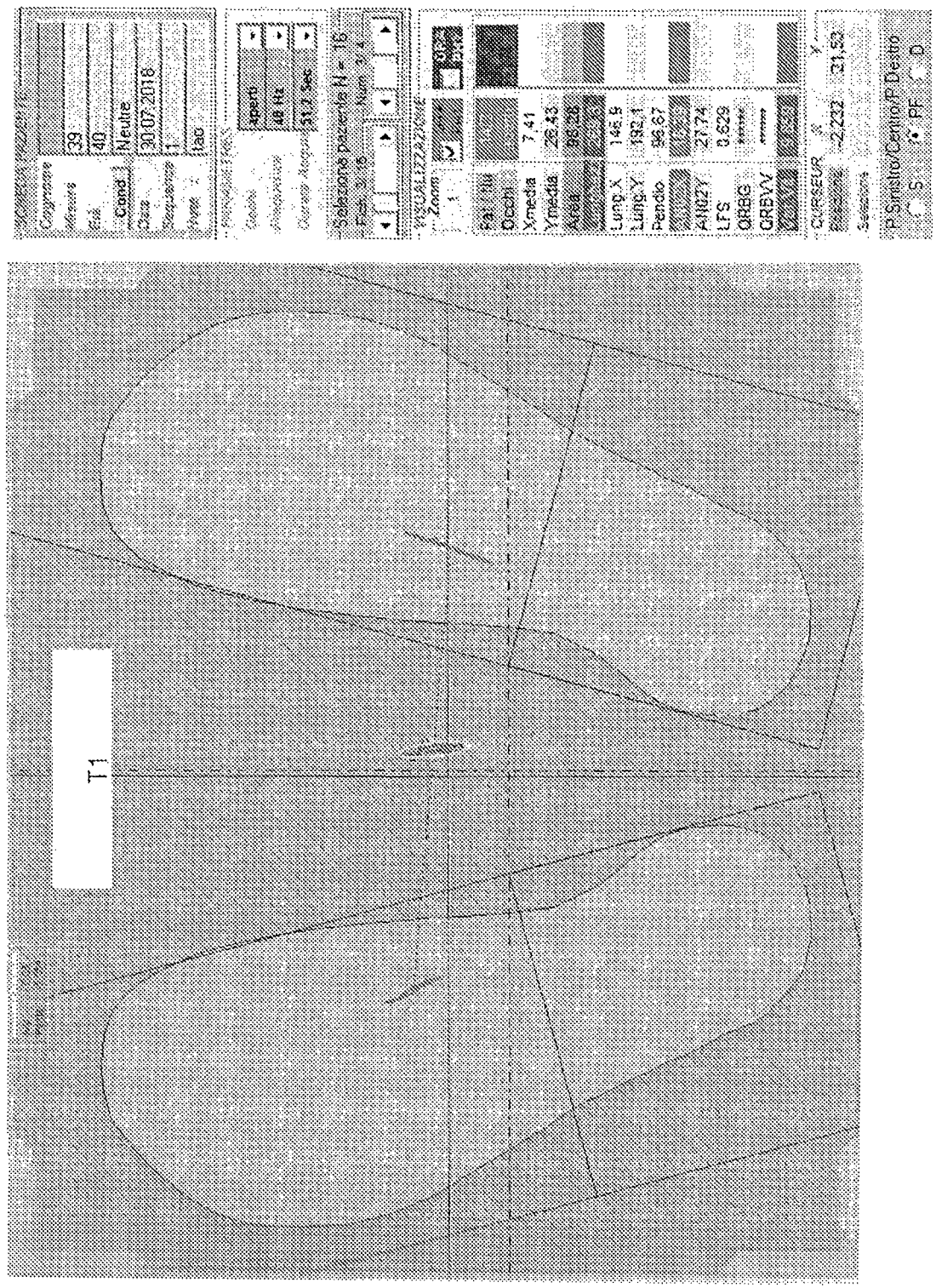

Third Example of an Application (FIGS. 9-11)

The application of the devices of the invention obtained an unexpected postural modulation. In fact, measuring, according to an assessment of the stabilometry (Cyber Sabot) compliant with the guidelines of the Ministry of Health regarding Posturology, the postural oscillations before (FIG. 9) and after (FIG. 10) the application of the devices of the invention to a patient suffering from rheumatic polymyalgia, we can see, as shown in the table in FIG. 11, that the area has significantly reduced from 359 sq. mm to 98 sq. mm (results measured immediately after only a few minutes of application). Therefore the application of the devices of the invention favours a considerable energy saving in the management of the upright posture; this energy remains available to the body that can use it for other metabolic functions.

Figure 12:
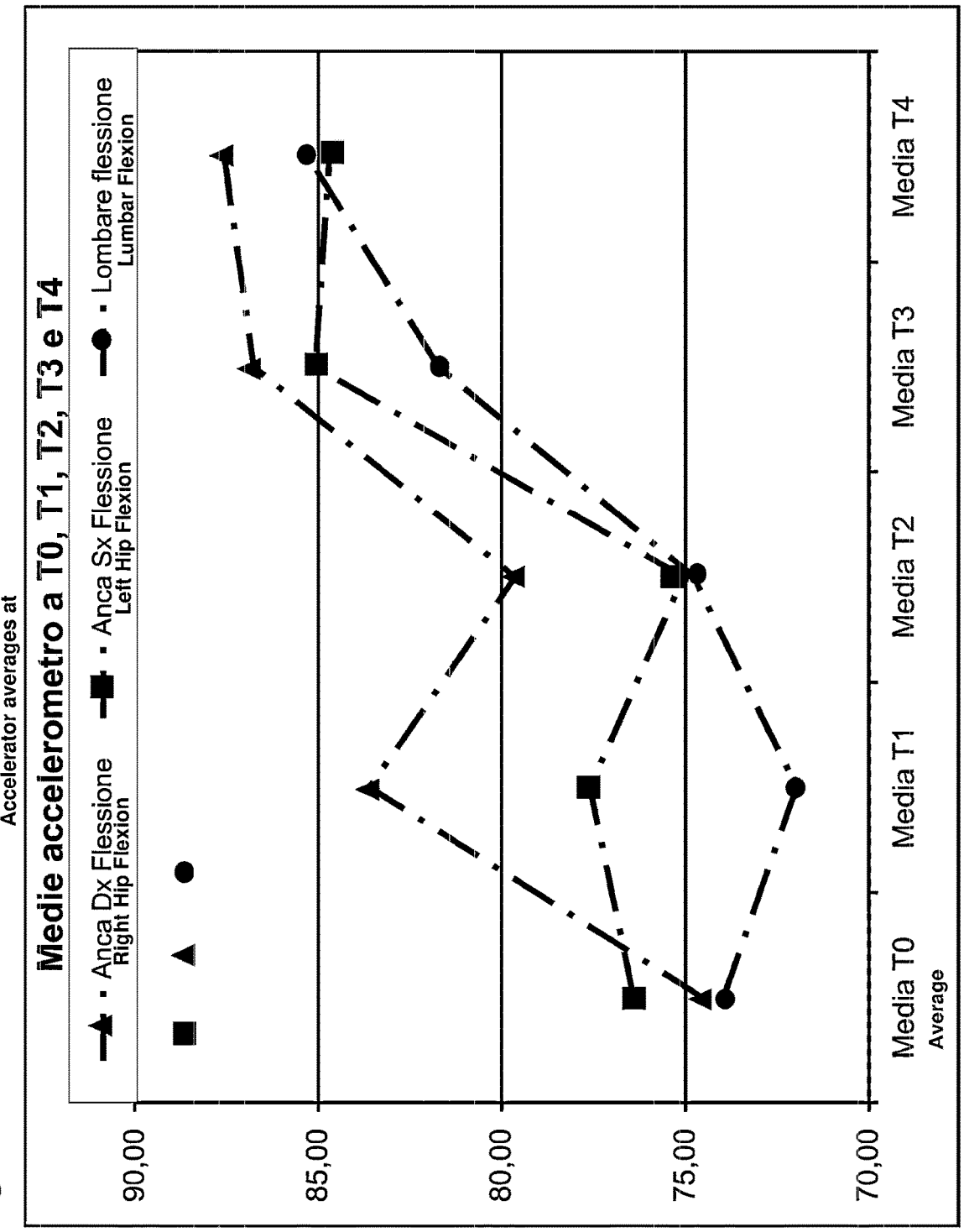
FIGS. 12-14 show the results regarding subjects with multiple sclerosis, on whom the devices of the invention have been used.
Figure 13:
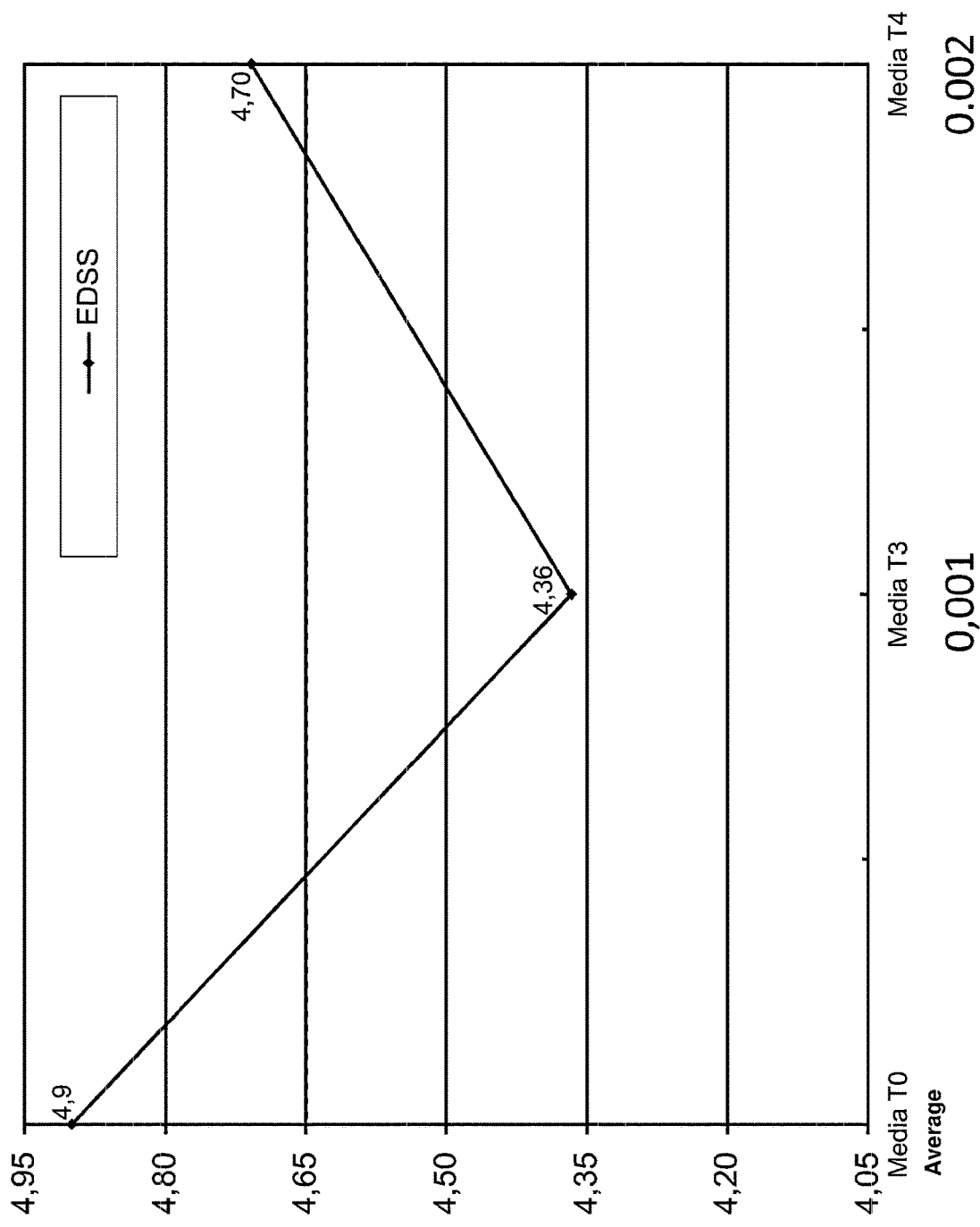
Figure 14:
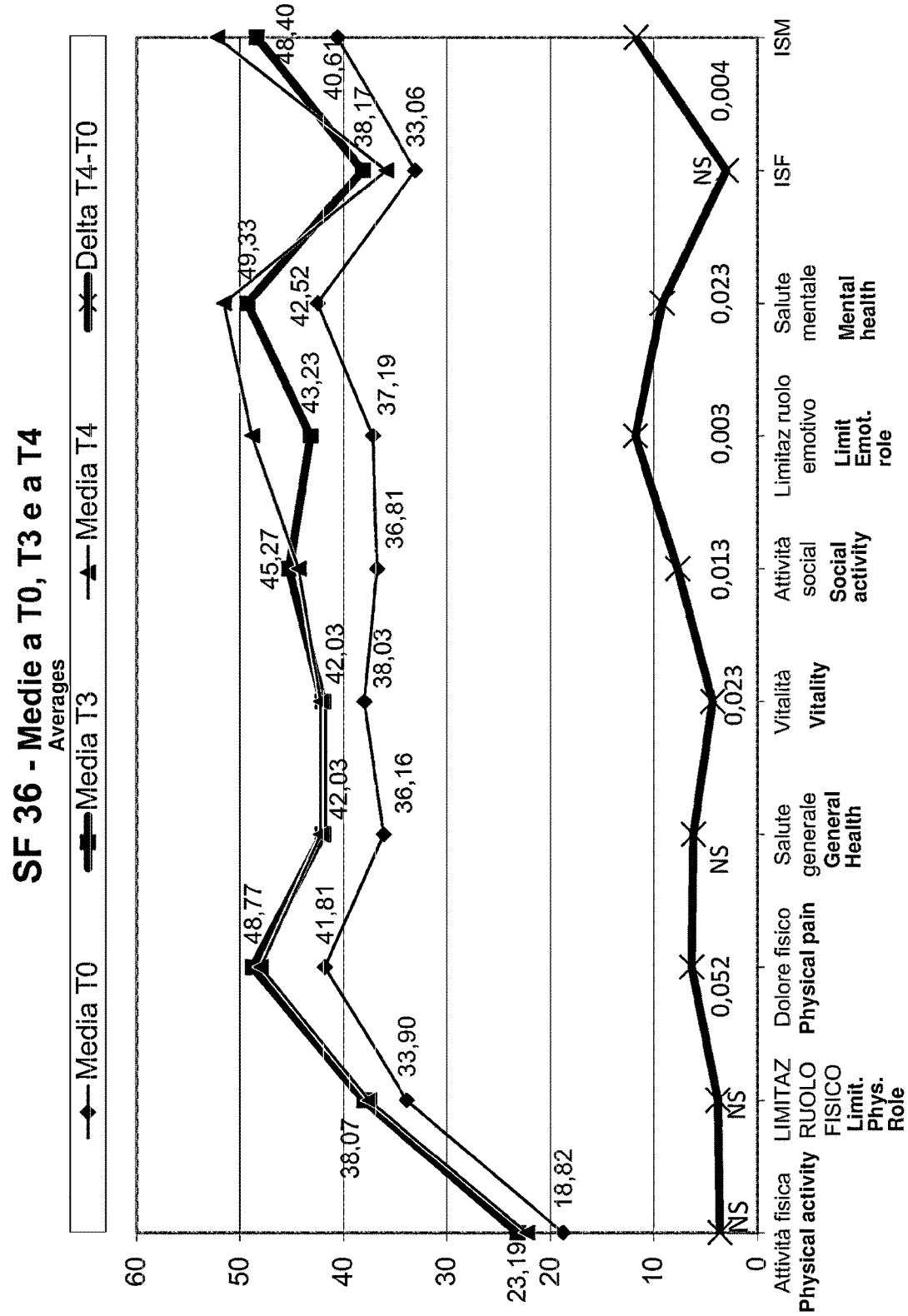

Fourth Example of an Application (FIGS. 12-14)

The results attained by the devices of the invention applied to people suffering from multiple sclerosis are surprising.

These results are evaluated according to:
The accelerometer test FIG. 12 on hip rotation, and lumbar flexion;
The calculation of the international EDSS index (Expanded Disability Status Scale—Disability scale used for patients with Multiple Sclerosis) FIG. 13;
The SF36 self-assessment test (questionnaire on the health of the patient) FIG. 14.
With reference to FIGS. 12-13-14:
T0 the condition of the patient without devices.
T1 30 minutes from the application of the devices of the invention;
T3 3 months from the application of the devices of the invention, with a continuous use of said devices;
T4 1 year from the application of the devices of the invention, with a continuous use of said devices.
Comments on the results.
Accelerometer test.

The diagrams, for the right hip flexion, the left hip flexion, and for the lumbar flexion, show a significant improvement from T0 to T4 of the flexion, i.e. the rotation capacity of the right hip ($p<0.05$) and the left hip ($p<0.01$), and even more significant increases in lumbar flexion (flex-extension) ($p<0.0009$).

It should be noted that the improvements are evident at 3 months (T3) and remain constant in the 1-year control period (T4), demonstrating the constancy of the effects.

EDSS

This index showed a significant improvement with an average of 4.9 at time T0 to 4.7 at time T4. This data is highly significant ($p<0.002$), especially considering that in these patients the data should have gotten worse over time.

SF36

With the SF36 self-assessment, patients demonstrated significant improvements at 3 months, which remained constant at one year.

The improvements were noted for the physical as well as the emotional and social spheres, but greater for the emotional-social spheres. In particular, there were improvements in physical activity, the limitation of the physical role, pain, general health, vitality and physical health index (PHI), as regards the physical sphere.

Social activities, the limitation of the emotional role, mental health and the mental health index (MHI) improved, as regards the emotional-social sphere.

The invention claimed is:

1. Therapeutic device to be applied to the skin in correspondence with the primary and secondary nerve endings of tendons, muscles, dermatomes and nerve endings, whose painful and inflammatory neuro-muscular and postural remodulation is to be favoured, including at least one laminar support element (1), and a mixture given by the combination of at least two types of quantum dots, including the following: (2)

Graphene quantum dots Code 900708 or quantum dots with a fluorescence indicatively corresponding to: $\lambda$ex 350 nm; $\lambda$em 445 nm, FWHM 65 nm, quantum yield >65%;

Graphene quantum dots blue luminescent Code 900726 or quantum dots with a fluorescence approximately corresponding to: $\lambda$ex 350 nm; $\lambda$em 445 nm±10 nm, FWHM 75 nm, quantum yield ≥20%

Graphene quantum dots cyan luminescent, Code 900707 or quantum dots with a fluorescence indicatively corresponding to: $\lambda$em 475-495 nm, FWHM 70 nm, quantum yield >17%

Graphene quantum dots aqua green luminescent, Code 900712 or quantum dots with a fluorescence indicatively corresponding to: $\lambda$ex 485 nm; $\lambda$em 530 nm±10 nm, FWHM 80 nm, quantum yield ≥17%;

Perovskite quantum dots oleic acid and oleylamine coated, Code 900747 or quantum dots with a fluorescence indicatively corresponding to: $\lambda$em 480 nm;

CdTe core-type quantum dots COOH functionalized Code 777978 or quantum dots showing a fluorescence indicatively corresponding to: $\lambda$em 710 nm, quantum yield ≥15%;

CdS/ZnS core-shell type quantum dots oleic acid functionalised Code 900286 or quantum dots showing a fluorescence indicatively corresponding to: $\lambda$max 385 nm $\lambda$em 400 nm±10 nm, quantum yield >50%;

CdS/ZnS core-shell type quantum dots oleic acid functionalised Code 900283 or quantum dots showing a fluorescence indicatively corresponding to:

$\lambda$max 405 nm $\lambda$em 425 nm±10 nm;

where said support consists of a laminar element of transparent material at the reference wavelengths and at the wavelength of radiation emitted by the human body, a first side of the laminar support (1) can be put in contact with the skin of the person whose dysfunction or inflammatory pathology is to be treated, and being placed on the opposite side of the first side of said support (1), or incorporated or diffused in the laminar element itself, a mixture of at least two of said quantum dots (2), with a concentration of 1 mg/cm2 to 100 mg/cm2, capable of emitting photons in the reference wavelength, with an intensity of between 0.1 mW/cm2 and 0.5 mW/cm2, and preferably between 0.2 mW/m2 and 0.4 mW/cm2, and the reference wavelength being between 280 nm and 740 nm, and preferably between 350 nm and 530 nm, when stimulated by at least one electromagnetic radiation infrared, luminous or ultraviolet tics.

2. Therapeutic device according to claim 1, characterised by the fact that said support (1) is made of a material that is transparent to at least one infrared, luminous, ultraviolet electromagnetic radiation, which excites the aforementioned mixture of quantum dots (2).

3. Therapeutic device according to claim 1, characterised by the fact that said support consists of a plastic material that can connect with the epidermis of the patient, and that is impermeable and inherent with respect to sweat of the skin.

4. Therapeutic device according to claim 1, characterised by the fact that said support is composed of a flexible material that can connect with the epidermis of the patient and follow its movements and/or deformations without detaching, preferably said support has a thickness between 0.05 mm and 2 mm, and even more preferably between 0.1 and 1 mm, being able to better adapt to the deformations of the epidermis.

5. Therapeutic device according to claim 1, characterised by the fact that said mixture of quantum dots (2) are arranged on the support (1) in a distributed manner occupying most of the surface of the side on which it is arranged, like a paint, exploiting the entire surface for a high transmission efficiency of said radiation, without being hindered by an overlap of the quantum dots, with a thickness between 0.001 and 1 mm.

6. Therapeutic device according to claim 1, characterised by the fact that said mixture of quantum dots (2) are arranged on the support (1) in discrete zones, concentrating the radiation flux in delimited zones, to be significantly intense to be received through said support, with thicknesses between 0.005 and 1 mm.

7. Therapeutic device according to claim 1, characterised by the fact that said laminar support element (1) is joined to a second laminar element (4, 5) for protection and confinement, comprising and confining said mixture of quantum dots (2), protecting it from external agents or mechanical stresses that would ruin it.

8. Therapeutic device according to claim 1, characterised by the fact that said second laminar element (4, 5) is made of a material that is transparent either to infrared radiation or to visible or ultraviolet light radiation, so that the radiation coming from outside and crossing said second laminar element (4, 5) can excite the aforementioned mixture of quantum dots (2) to emit the frequencies of interest.

9. Therapeutic device according to claim 1, characterised by the fact that said protection (4, 5), with an extension comparable to the extension of the support (1), is associated against it with the surface of its side facing the support (1), holding and confining hermetically sealing the mixture of quantum dots (2).

10. Therapeutic device according to claim 1, characterised by the fact that the protection (4, 5) is composed of a transparent protective ink or a plastic film that can reduce the thickness of the device, thereby making it easier to wear.

11. Therapeutic device according to claim 1, characterised by the fact that said mixture of quantum dots (2) is diluted within an ink in order to be printed on the support (1) or on the protection (4, 5), directly on the mutually facing sides.

12. Therapeutic device according to claim 1, characterised by the fact that said ink is a transparent ink, so that only the characteristics of the adhesive and the ink are carried out in the dispersion medium, and that all the outgoing photon emissions and the incoming radiations can reach, with minimal attenuation, the mixture of quantum dots.

13. Therapeutic device according to claim 1, characterised by the fact that the total thickness of the device is kept to a minimum to maintain a high level of elasticity and so it can adapt to the surface stresses of the skin without cracking, breaking or tearing.

14. Therapeutic device according to claim 1 characterised by the fact that the mutual connection between the dermis and the support and/or the support and the protection is obtained by means of a flexible double-sided adhesive material (3).

15. Therapeutic device according to claim 1 characterised by the fact that the device can be for the most part transparent, and connecting with an adhesive effect on the skin, placed near primary and secondary endings, tendons, muscles, dermatomers, nerve endings, to favour a neuromuscular and postural remodulation, it makes it possible to check for any redness of the skin.

16. Therapeutic device according to claim 1, characterised by the fact that the wearable therapeutic device exerts a greater activity of the mixture of quantum dots (2) with an ink comprising 5 to 80% of carbon nanotubes, with a mixture of quantum dots from 95 to 20%, depending on the type of quantum dots used and the frequency of interest of the therapeutic radiation, managing to calibrate, redefine and dose the quantity of photons emitted by the device according to the needs of the patient and the desired stimulus.

17. Therapeutic device according to claim 1, characterised by the fact that a mixture given by the combination of at least two types of quantum dots, from the following: (2)

Graphene quantum dots Code 900708 or quantum dots with a fluorescence indicatively corresponding to: λex 350 nm; λem 445 nm, FWHM 65 nm, quantum yield >65%;

Graphene quantum dots blue luminescent Code 900726 or quantum dots with a fluorescence approximately corresponding to: λex 350 nm; λem 445 nm±10 nm, FWHM 75 nm, quantum yield ≥20%

Graphene quantum dots cyan luminescent, Code 900707 or quantum dots with a fluorescence indicatively corresponding to: λem 475-495 nm, FWHM 70 nm, quantum yield ≥17%

Graphene quantum dots aqua green luminescent, Code 900712 or quantum dots showing a fluorescence indicatively corresponding to: λex 485 nm; λem 530 nm±10 nm, FWHM 80 nm, quantum yield≥17%;

Perovskite quantum dots oleic acid and oleylamine coated, Code 900747 or quantum dots with a fluorescence indicatively corresponding to: λem 480 nm;

CdTe core-type quantum dots COOH functionalized Code 777978 or quantum dots with a fluorescence indicatively corresponding to: λem 710 nm, quantum yield ≥15%;

CdS/ZnS core-shell type quantum dots oleic acid functionalised Code 900286 or quantum dots showing a fluorescence indicatively corresponding to: λmax 385 nm λem 400 nm±10 nm, quantum yield>50%;

CdS/ZnS core-shell type quantum dots oleic acid functionalised Code 900283 or quantum dots with a fluorescence indicatively corresponding to: ∧max 405 nm λem 425 nm±10 nm;

reaches and produces the same wavelengths as ULLLT (ultra-low-level laser therapy) but with ultra-low intensity, with an intensity between 0.1 mW/cm2 and 0.5 mW/cm2, and preferably between 0.2 mW/cm2 and 0.4 mW/cm2.

* * * * *